United States Patent [19]

Barnes

[11] Patent Number: 4,758,081

[45] Date of Patent: Jul. 19, 1988

[54] CONTROL OF LASER PHOTOCOAGULATION USING RAMAN RADIATION

[75] Inventor: Clarence W. Barnes, San Francisco, Calif.

[73] Assignee: Bausch & Lomb Incorporated, Rochester, N.Y.

[21] Appl. No.: 756,862

[22] Filed: Jul. 18, 1985

[51] Int. Cl.$^4$ .......................... A61B 3/10; A61B 17/36
[52] U.S. Cl. .................................. 351/221; 128/303.17
[58] Field of Search ...................... 351/221; 128/303.1, 128/303.13, 303.17

[56] References Cited

PUBLICATIONS

Robert Alexander Weale, "Vision and Fundus Reflectometry", Doc. Opthalm., vol. 19, 1965, pp. 252–286.
W. Hunold et al, "Spectrophotometric Determination of the Melanin Pigmentation of the Human Ocular Fundus in vivo", Opthal. Res. vol. 6, 1974, pp. 355–362.
R. Birngruber et al, "Fundus Reflectometry: A Step Towards Optimization of the Retina Photocoagulation", Mod. Probl. Opthal., vol. 18, 1977, pp. 383–390.
M. L. Wolbarsht et al, "Lasers in Opthalmology: The Path from Theory to Application", Applied Optics, vol. 18, No. 10; May 15, 1979, pp. 1516–1526.
O. Pomerantzeff et al, "A Method to Predetermine the Correct Photocoagulation Dosage", Arch. Opthalmol., vol. 101, Jun. 1983, pp. 949–953.
O. Pomerantzeff et al, "Time and Location Analysis of Lesion Formation in Photocoagulation", Arch. Opthalmol., vol. 101, Jun. 1983, pp. 954–957.
Weinberg et al, "Controlling Retinal Photocoagulation by Light Reflection", Docum. Opthal. Proc. Series, vol. 36, ed. by R. Birngruber and V. P. Gabel, c. 1984, Dr. W. Junk Publishers, The Hague, pp. 299–311.
O. Pomerantzeff et al, "Toward Automation in Photocoagulation", in Docum. Opthal. Proc. Series, vol. 36, ed. by R. Birngruber and V. P. Gabel, c. 1984, Dr. W. Junk Publishers, The Hague, pp. 313–319.
G. Peyman et al, "Ocular Effects of Various Laser Wavelengths", Survey of Opthalm., vol. 28, No. 5, Mar.-Apr. 1984, pp. 391–404.
O. Pomerantzeff et al, "Automation in Krypton Laser Photocoagulation", Investigative Opthalmology and Visual Science, vol. 25, Jun. 1984, pp. 711–719.
W. Weinberg et al, "The Change in Light Reflection of the Retina During Therapeutic Laser-Photocoagulation", IEEE J. Quantum Electronics, vol. QE-20, No. 12, Dec. 1984, pp. 1481–1489.

Primary Examiner—John K. Corbin
Assistant Examiner—P. M. Dzierzynski
Attorney, Agent, or Firm—John S. Norton

[57] ABSTRACT

Apparatus is disclosed for pre-determining laser coagulation dosages and for monitoring laser photocoagulation during treatment by detection of radiation produced in the eye. Embodiments of the present invention comprise means for applying radiation to a target in an eye (1, 2, 3, 5, 6, 7 and 9) and means for detecting the radiation produced by the target having wavelengths different from the wavelength of the applied radiation (4, 200, 12 and 13). In various embodiments, the radiation produced by the target is fluorescence radiation, Raman radiation, two photon excitation radiation and so forth.

2 Claims, 1 Drawing Sheet

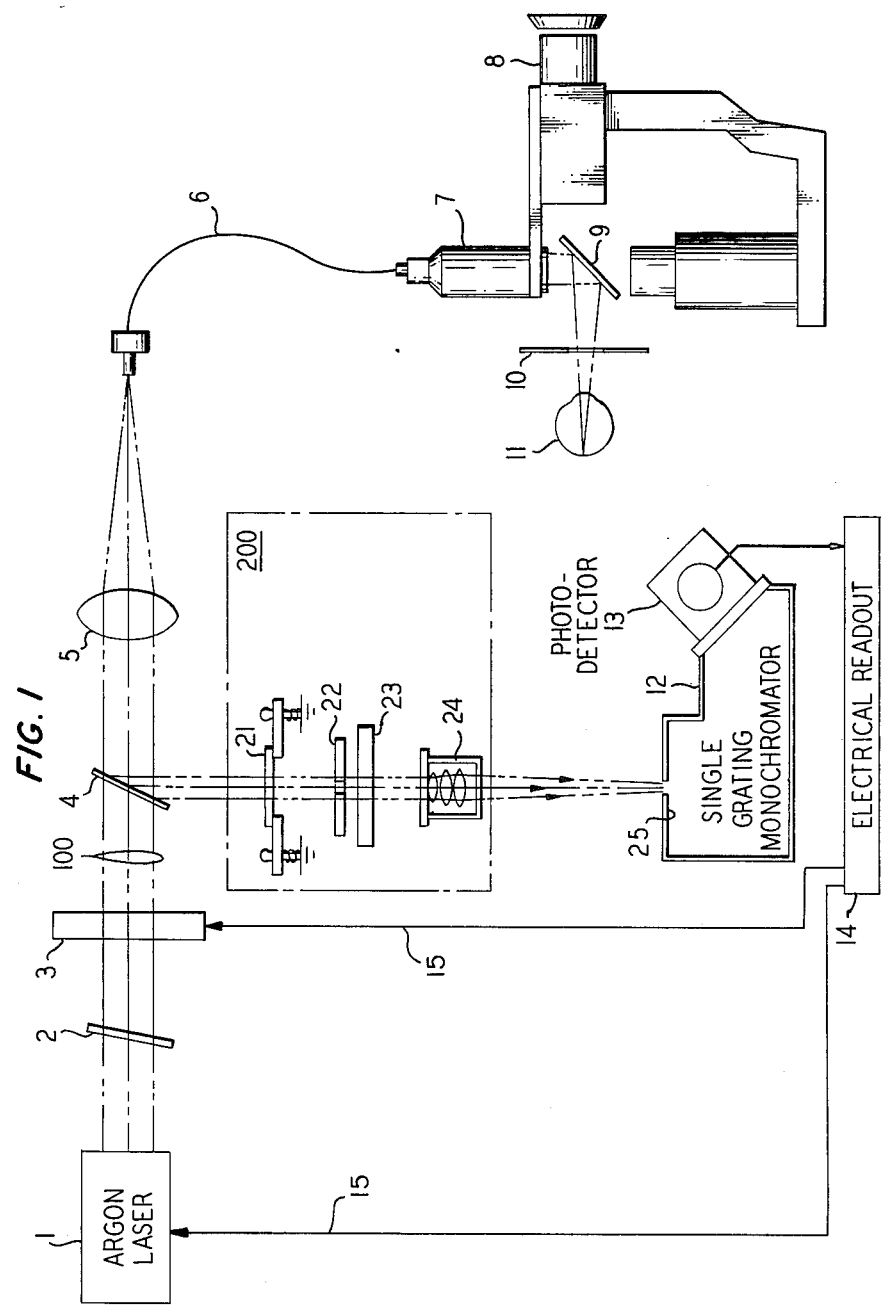

CONTROL OF LASER PHOTOCOAGULATION USING RAMAN RADIATION

TECHNICAL FIELD

The present invention pertains to the field of laser photocoagulation and, in particular, to apparatus for predetermining laser coagulation dosages and for monitoring laser photocoagulation by detection of secondary radiation.

BACKGROUND ART

Laser photocoagulators have become an important tool in treating eye disease. As stated in an article entitled "Lasers In Ophthalmology: The Path From Theory To Application" by M. L. Wolbarsht and M. B. Landers III in *Applied Optics,* Vol. 18, No. 10, May 15, 1979, pp. 1516-1526, specifically at p. 1516:

"The argon laser photocoagulator is routinely used by ophthalmologists all over the world and is now standard practice for the treatment of many retinal diseases. Indeed for some problems such as diabetic retinopathy, not to use it borders on malpractice."

Although retinal photocoagulation has been used since before the advent of lasers and is now a standard treatment of choice for some common retinal disorders, the occurrence of complications is high, compared to other kinds of laser therapy. Because of variations in vascularization and pigmentation from place to place on the fundus, obtaining an optimum application of laser energy requires a delicate adjustment of laser energy, laser pulse duration, and lower beam spot size. An exposure which is therapeutic in one location may be ineffective in another, and may produce a hemorrhage in yet another.

Current clinical practice relies on visual assessment of pigmentation and vascularization and upon visual estimates of coloration changes that occur after a treatment pulse. However, such visual assessments are recognized by the art to be inadequate for reliable determination of the optimal laser application. Furthermore, there is recognition in the art of the need for a means of monitoring laser photocoagulation during treatment. As stated in an article entitled "Fundus Reflectometry: A Step Towards Optimization Of The Retina Photocoagulation" by R. Birngruber, V. -P. Gabel and F. Hillenkamp in *Mod. Probl. Ophthal.,* vol. 18, 1977, pp. 383-390 at p. 383:

"Improvements in clinical retinal photocoagulation can be achieved by both the optimal adaptation of the instrument to the problem, and variation of the physical irradiation parameters.... It is obvious from the theory of heat conduction, that in the range of exposure times from $10^{-3}$ to 10 sec of interest here, the energy necessary for a given reaction in the irradiated area decreases markedly with shorter times.... It is understood though, that the possibility of manual control of the effect through visual observation of the coagulation site ceases for exposure times below about 1 sec.

Monitoring the time development of the retinal blanching during and after coagulation with suitable photodetectors should result in a more direct measure of the influence of the important parameters such as energy and exposure time on the retinal reaction. Such a technique could moreover eventually lead to a method for an automatic control of exposure times, even for very short times."

In searching for a means of monitoring the progress of laser photocoagulation during treatment, it has been recognized in the art that there is a connection between reflectivity of the irradiated tissues and the effects of the photocoagulation, see for example an article entitled "Time And Location Analysis Of Lesion Formation In Photocoagulation" by Oleg Pomerantzeff, Guang-Ji Wang, Michail Pankratov, and Julianne Schneider in *Arch. Ophthalmol.,* Vol. 101, June, 1983, pp. 954–957. This has suggested the use of reflectometry, i.e. measurement of light backscattered from an illuminated spot on the retina, to monitor photocoagulation. The reflected light could come from the photocoagulation laser itself or from a secondary pilot laser.

In addition to attempts to monitor laser photocoagulation during treatment, there have been attempts in the art to pre-determine the appropriate laser dosages to apply for treatment of specific diseases. These attempts have used reflectometry to determine the laser parameters. Such a use of reflectometry is illustrated in an article entitled "A Method To Predetermine The Correct Photocoagulation Dosage" by Oleg Pomerantzeff, Guang-Ji Wang, Michail Pankratov, and Julianne Schneider in *Arch. Ophthalmol.,* Vol. 101, June 1983, pp. 949–953, at p. 949:

"The most common goal of photocoagulation in the macular area is closing leakage from very small vessels and destroying new-formed vessels in the sub-retinal space.... Yellow and green light are recommended for treatment of the macula since the yellow pigment in the inner layers of this area absorbs very little of these colors.... The reaction of retinal tissue to the irradiation with a given power density varies according to the local concentrations of blood and melanin. Therefore, to avoid overtreatment and the risk of hemorrhage, it is desirable to know this relative concentration in the target tissues before treatment is applied, especially when red light is used. In this study, we suggest a possible method to measure this relative concentration.

Absorbance cannot be measured directly in a living eye but it can be measured indirectly by measuring reflectance. To do this we assume that the light that is neither absorbed by nor scattered back from the retinal or chloroidal layers reaches the sclera, which transmits only a negligible percentage, and is reflected from it. This reflected light is partly absorbed on its way back, and finally emerges from the retina into the vitreous. Therefore, if we measure the power applied to the retina and the power emerging back from the retina, the difference between the two is a measure of the absorbance in the retina and choroid. In photocoagulation it is also important to determine, if possible, the level within which most of the melanin is concentrated."
at p. 950:

"Since the reflection by the retinal structures is most diffuse, we are obviously not collecting all the light reflected from the retina. However, we may assume that the ratio of the collected to the reflected light remains the same, at least in the same eye."
and at p. 952:

"Not all the light emerging from the cornea is diffusely reflected. There are also some discrete specular reflections that may eventually fail into the entrance pupil of the measuring system, making the measurements unreliable.... The reflectance, and consequently the absorbance, depends not only on the retinal area and the selected wavelength, but also on the angle at which the particular structure is irradiated. Therefore the absorbance should be measured using the coagulating beam in its coagulating position."

In sum, fundus reflectometry, i.e. measurement of light that is backscattered from an illuminated spot on the retina, is used in the art to pre-determine laser photocoagulation dosages as well as to monitor laser photocoagulation during treatment. In theory, if the intensity of the incident radiation is known, the absorbance of the tissue can be calculated from the reflectance, and if the absorbance is known, the amount of energy absorbed from a treatment can be predicted. However, application of this theory involves a number of complications, such as: (1) wavelength dependence of the scattering, (2) angular dependence of the scattering, (3) the relation between the scattered light which leaves the pupil of the eye and is therefore accessible for measurement and the scattered light which is re-absorbed inside the eye and therefore cannot be directly measured. Furthermore, in prior art apparatus constructed to apply fundus reflectometry, reflection of the incident light from filters, lenses and other optical transmission components is quite strong, being at least a few percent of the incident radiation. This means that simple reflectance from a target cannot be easily measured when the same optical system is used to deliver the light to the target and to capture the reflected light. However, when two separate optical systems are used for simple reflectance measurement, it is difficult to insure that they are both aimed at precisely the same target spot.

DISCLOSURE OF INVENTION

The above-described problems occurring in the use of reflectometry for pre-determining appropriate laser dosages for laser photocoagulation and for monitoring laser photocoagulation during treatment are advantageously solved by embodiments of the present invention.

Embodiments of the present invention comprise means for applying radiation to a target in an eye and means for detecting radiation produced by the target having wavelengths different from the wavelength of the applied radiation. Such radiation produced by the target is denoted hereinafter as non-Rayleigh radiation (NRR). In various embodiments, the NRR is fluorescence radiation, Raman radiation, two photon excitation radiation and so forth. Furthermore, in a first embodiment, the means for applying radiation to the target spot is the laser coagulation source itself; in other embodiments the application means comprises one or more laser sources other than the laser coagulation source; and in still further embodiments the application means comprises means, cooperating with the laser coagulation source, to provide laser radiation.

Embodiments of the present invention can be used to pre-determine the effect of the laser coagulation by measuring absorbance prior to treatment and also to monitor the laser coagulation during treatment.

BRIEF DESCRIPTION OF THE DRAWING

A complete understanding of the present invention may be gained by considering the following detailed description in conjunction with the accompanying drawing in which:

FIG. 1 shows, in pictorial form, an apparatus constructed in accordance with the present invention.

PREFERRED EMBODIMENT FOR CARRYING OUT THE INVENTION

When optical radiation strikes a target, such as the fundus of the eye, some of the radiation is transmitted, some is scattered and some is absorbed. The fundus is a complex optical system consisting of several different kinds of pigments arranged in a layered structure. It comprises a highly non-uniform distribution of particles and surfaces which absorb, scatter, and reflect light. Nevertheless, it is possible to measure the amount of light absorbed by the fundus by measuring the amount of light that is backscattered or reflected. Since light is scattered at all angles, only a fraction passes back out through the pupil where it can be measured. But, by making some reasonable assumptions about the angular distribution of scattering, estimates of fundus absorption can be made from measurements of light that is scattered back out through the pupil of the eye.

The physical mechanisms responsible for scattering of light from molecules provide that when light of a first wavelength strikes a molecule, most of the scattered radiation is at exactly the same wavelength. Such scattered radiation (e.g. reflected radiation) is called Rayleigh radiation. However, some scattered radiation occurs at wavelengths different from the first wavelength, denoted hereinafter as NRR. In fluorescence, for instance, radiation is absorbed and re-radiated at many different wavelengths. In Raman scattering, radiation is produced which has a relatively small change in wavelength from the incident radiation, such Raman radiation being characteristic of the scattering molecule. Raman radiation may have wavelengths longer than the first wavelength, i.e. "Stokes" Raman radiation, or it may have wavelengths shorter than the first wavelength, i.e. "anti-Stokes" Raman radiation. Both Stokes and anti-Stokes Raman radiation are typically much smaller in intensity than Rayleigh radiation. Furthermore, anti-Stokes Raman radiation is typically much less intense than Stokes Raman radiation. There are, however, some circumstances in which both types of Raman radiation may become very much stronger than usual. In particular, this occurs when the wavelength of the indicent radiation coincides with an absorption band of the molecule. In this instance, resonance Raman scattering occurs with an intensity many orders of magnitude greater than normal Raman scattering.

I have discovered that apparatus for pre-determining laser dosage and for monitoring laser coagulation can advantageously be provided by monitoring NRR, and Raman radiation in particular. An important reason for this advantage is the fact that this radiation is produced mainly in the target (Glasses used in lenses and optical fibers may produce fluorescence and Raman radiation. Moreover, certain tissues in the eye, such as the lens, may produce NRR. However, the levels of NRR produced by such sources would ordinarily be very small in comparison with the NRR from the target and may be regarded as a negligible "background" signal). Consequently, by detecting NRR instead of Rayleigh radiation, background scattering from optical transmission components and areas of the eye other than the target is significantly reduced.

Embodiments of one aspect of the present invention comprise a laser coagulation source, a beam delivery system for transmitting laser radiation from the source to the laser coagulation target spot on the retina, and an NRR monitor which receives the NRR from the laser coagulation target spot on the retina after it is transmitted back through the beam delivery system. A major advantage of such an embodiment, obtained by using the same optical system for delivering the light to the target spot and for monitoring the backscatter therefrom, is that the same target spot is "seen" by the delivery and the monitoring systems. Such embodiments are useful for monitoring during treatment because they provide NRR detection at the same time that laser coagulation radiation is being applied for treatment. The NRR is detected by an apparatus, such as a monochromator, which is tuned to select suitable NRR and to reject the strong Rayleigh radiation. This provides a scattering response with a sufficiently high signal-to-noise ratio as to be useful in estimating target absorbance.

FIG. 1 shows an embodiment of the present invention where laser source 1 is a 5 watt, CW argon ion, Spectra Physics Argon laser, model no. 164/168. Laser radiation produced by laser source 1 impinges upon filter 2. Filter 2 selects the 514.5 nm line and passes the filtered radiation as beam 100, which filtered radiation is used for photocoagulation. The filtered radiation in beam 100 passes through shutter 3 in order to form a pulse for coagulation. The pulse of radiation then passes through beam splitter 4 and is focused by lens 5, for example, an 18 mm focal length lens, into optical fiber 6, for example, a Fiberguide Industries, Inc. fiberoptic cable 80/125 (denoting core/cladding diameter in microns).

The filtered radiation, output from cable 6, impinges upon zoom lens 7 (for example, Chugai Boyeki Company, Ltd. Model No. M10Z118 zoom lens), which zoom lens is held by slit lamp 8, for example, a Zeiss slit lamp. Zoom lens 7 is used in this embodiment to allow a physician to vary the spot size of the laser radiation on the target in the eye and the slit lamp is provided as a light source for the physician to examine the eye.

The radiation emerging from zoom lens 7 impinges on mirror 9 where it is diverted through shutter 10, for example, a black anodized aluminum shutter, and from there into eye 11 of a patient. In an instrument designed solely for clinical photocoagulation, shutter 10 would not normally be present. Photocoagulation pulses would be controlled only with shutter 3, as mentioned previously hereinabove.

Carotenoid retinal pigments in the eye generate Raman radiation having a frequency shift of approximately 1500 cm$^{-1}$ from the 514.5 nm laser excitation. This corresponds to a Stokes radiation wavelength of 558 nm when the laser excitation is at 514.5 nm. Thus, NRR, including Raman radiation in the 1500 cm$^{-1}$ Stokes band at 558 nm, is generated in eye 11 and directed back through the above-described system to impinge upon beam splitter 4. Beam splitter 4 directs the backscattered radiation, containing mostly radiation at the wavelength of laser source 1 along with relatively weak NRR, through band rejection filter 200 and into monochromator 12. In this embodiment, monochromator 12 should be tunable so as to cover wavelengths in the range of roughly 2000 cm$^{-1}$ on either side of the 514.5 nm argon laser line. Furthermore, it must have a very high rejection ratio for the 514.5 nm Rayleigh radiation background.

The radiation impinging upon monochromator 12 is stripped of 514.5 nm Rayleigh reflected light by 514.5 nm band rejection filter 200. As shown in FIG. 1, band rejection filter 200 comprises Omega, Inc. optical filter 21, one millimeter slit 22, Oriel, Inc. Model No. 5748 variable interference filter 23, and Edmund Scientific Corporation "Edscorp $\times$15" microscope eyepiece focusing lens 24. Lens 24 focuses the radiation emerging from band rejection filter 200 onto 0.006 inch wide entrance slit 25 in single grating monchromator 12. RCA 931B photomultiplier tube photodetector 13 receives the output from monchromator 12 and, in response thereto, provides an electrical output signal to electrical readout 14. In various embodiments electrical readout 14 may comprise strip-chart recorders or microprocessors or other types of computers and the like for evaluating the output of photodetector 13.

During therapeutic photocoagulation, retinal tissue undergoes changes in optical characteristics that include changes in the level of Raman backscatter. This change is monitored by electrical readout 14. The resulting electrical signal provides an objective measurement of the degree of tissue photocoagulation at each instant, and may be used to modulate the laser intensity to achieve an optimum treatment. The evaluation of the changes may involve comparing previous readings, then making a decision based thereon and thereafter resetting the output of laser source 1 during treatment or establishing appropriate settings for the output of laser source 1 for subsequent treatment. Furthermore, the laser pulses may be controlled by varying the response of shutter 3 to increase or decrease the laser pulse duration or intensity, and so forth. The control of laser source 1 or shutter 3 discussed hereinabove may be performed by applying signals 15 from electrical readout 14 directly to laser source 1 and/or shutter 3. It should be clear to those skilled in the art that various other means for controlling the intensity, duration and placement of the laser coagulation radiation in response to output from electrical readout 14 may be constructed without departing from the spirit and scope of the present invention.

Embodiments of the present invention may also be used to measure the temperature of laser irradiated tissue. This is done by tuning the NRR detector to detect anti-Stokes Raman radiation. For the specific example of argon laser 514.5 nm input, the anti-Stokes radiation corresponds to a wavelength of 478 nm. The anti-Stokes radiation is weaker than the Stokes radiation, however its intensity is proportional to the population of the first vibrational level of the Raman-active molecules. Since the population of this vibrational level increases with temperature according to the Boltzman law, a measurement of the intensity of the anti-Stokes radiation may be used to calculate temperature. Further, the duration, intensity and position of the laser coagulation pulse may be controlled in response to the temperature in the manner described hereinabove.

Clearly, many other varied embodiments may be constructed by those skilled in the art without departing from the spirit and scope of the present invention.

I claim:

1. Apparatus for applying laser radiation to a target in an eye and for monitoring the progress of resultant photocoagulation which comprises:
    a laser source,
    a fiber optic cable for receiving laser radiation and transmitting it to said target,
    means for detecting backscattered Raman radiation from the target, said means comprising a beamsplitter, a band rejection filter, a monochromator and a photodetector, said beamsplitter being disposed to direct the backscattered Raman radiation from the target through said band rejection filter which strips Rayleigh reflected light from the Raman radiation and transmits the latter to the monochromator, and said photodetector functioning to receive the output from the monochromator and provide an electrical signal indicative of the level of Raman backscatter from the target and of the resultant photocoagulation.

2. Apparatus according to claim 1 wherein the detecting means is tuned to detect the relative intensities of Stokes and anti-Stokes radiation and functions to compute the temperature of the lasers irradiated target.

* * * * *

UNITED STATES PATENT AND TRADEMARK OFFICE
CERTIFICATE OF CORRECTION

PATENT NO. : 4,758,081
DATED : July 19, 1988
INVENTOR(S) : Clarence W. Barnes

It is certified that error appears in the above-identified patent and that said Letters Patent are hereby corrected as shown below:

Col. 1, line 33, before "beam" delete "lower" and substitute --laser--.

Col. 2, line 44, delete "chloroidal" and substitute --choroidal--.

Col. 2, line 63, delete "fail" and substitute --fall--.

Col. 8, line 7, delete "lasers" and substitute --laser--.

Signed and Sealed this

Fourteenth Day of February, 1989

*Attest:*

DONALD J. QUIGG

*Attesting Officer*      *Commissioner of Patents and Trademarks*